(12) United States Patent
Rouiller et al.

(10) Patent No.: US 6,752,626 B1
(45) Date of Patent: Jun. 22, 2004

(54) DEVICE AND METHOD FOR REGISTERING THE USE OF AN ODONTOLOGICAL INSTRUMENT

(76) Inventors: Jean-Claude Rouiller, Rue Abraham-Robert 49, CH-2300 La Chaux-de-Fonds (CH); Olivier Breguet, 2, chemin de Jolimont, CH-2400 Le Locle (CH)

( * ) Notice: Subject to any disclaimer, the term of this patent is extended or adjusted under 35 U.S.C. 154(b) by 205 days.

(21) Appl. No.: 10/049,146
(22) PCT Filed: Jul. 31, 2000
(86) PCT No.: PCT/CH00/00411
§ 371 (c)(1), (2), (4) Date: Apr. 16, 2002
(87) PCT Pub. No.: WO01/10329
PCT Pub. Date: Feb. 15, 2001

(30) Foreign Application Priority Data

Aug. 6, 1999 (FR) .............................. 99 10348

(51) Int. Cl.$^7$ .............................. A61C 3/00; A61C 19/04
(52) U.S. Cl. .............................. 433/27; 433/72; 433/102
(58) Field of Search .............................. 433/27, 72, 102, 433/165; 73/783, 760

(56) References Cited

U.S. PATENT DOCUMENTS

| 4,733,361 A | 3/1988 | Krieser et al. .............. 364/508 |
| 4,882,867 A | 11/1989 | Linden .......................... 40/625 |
| 4,900,252 A * | 2/1990 | Liefke et al. ................. 433/27 |
| 5,414,777 A | 5/1995 | van der Schaar et al. .. 352/142 |
| 5,464,362 A | 11/1995 | Heath et al. .................. 451/48 |
| 5,628,674 A | 5/1997 | Heath et al. .................. 451/48 |
| 6,128,966 A * | 10/2000 | Usui et al. ................. 73/865.8 |
| 6,358,051 B2 * | 3/2002 | Lang et al. ................. 433/173 |
| 6,464,497 B2 * | 10/2002 | Landoz ........................ 433/77 |
| 6,547,565 B1 * | 4/2003 | Dawood et al. ............ 433/174 |
| 2003/0186188 A1 * | 10/2003 | Tinnin ........................ 433/77 |

* cited by examiner

Primary Examiner—Cary E. O'Connor
(74) Attorney, Agent, or Firm—Davis & Bujold, PLLC

(57) ABSTRACT

The invention concerns a device comprising a mechanism for indicating a value representing current fatigue and devices for modifying the value based on parameters related to the use of the odontological instrument. In a particular embodiment, the devices indicating the fatigue value comprises a washer (16) connected to the instrument and provided with a certain predetermined number of detachable elements or pre-perforations (17). Depending on the use of the instrument, for example, its diameter, its taper ratio, the curve of the dental canal to be excavated and the duration of the operation, a certain number of detachable elements are removed or a certain number of pre-perforations are perforated (17'). When the number of detachable elements or the number of pre-perforations (17) remaining on the device is less than the number of elements to be detached or perforated on the basis of the predetermined operational parameters, the odontological instrument should no longer be used. The device enables the odontological instrument to avoid being broken in a dental canal.

15 Claims, 2 Drawing Sheets

DEVICE AND METHOD FOR REGISTERING THE USE OF AN ODONTOLOGICAL INSTRUMENT

FIELD OF THE INVENTION

The present invention concerns a device and a method for indication the current fatigue of a odontological instrument having at least a cutting zone and a handle.

BACKGROUND OF THE INVENTION

In the odontological field surgeons use various instruments to excavate the dental canal before the introduction of a filling material into said dental canal.

The instruments to excavate the dental canal have to satisfy very high requirements. They must be sharp on at least a part of their length and their distal end have to be guided easily in the dental canal even when the canal has a small curve radius. To avoid the odontological instruments being broken in a dental canal they are mainly used manually rather than driven by a motor. Furthermore the screwing effect has to be avoided to reduce the tensions inside of the instruments. For these reasons this kind of instruments are known to be delicate.

In U.S. Pat. No. 5,628,674 it is known that a nickel and titanium alloy is adequate for the manufacturing of these instruments. It permit the realization of tools being resistant and supple allowing the use of motor driven odontological instruments. The instruments made of this alloy have an important drawback. Due to their resilience and their suppleness, the instruments do not present any lasting distortion indicating that they must be replaced. They remain identical and keep their aspect even when the limit of fatigue is reached. When the current fatigue becomes to high the instruments brake without showing any visible sign permitting to predict the moment when the braking occurs. Therefore the use of this type of instruments represent a number of serious problems for surgeons.

SUMMARY OF THE INVENTION

The object of the present invention is to overcome all these drawbacks and to realize a device permitting to give in a simple way an indication corresponding to the fatigue of an instrument, so that a user could replace the same before it represents a risk of breaking.

This object is reached by the device of the invention, characterized in that it comprises means connected to said odontological instrument indicating a value representing the current fatigue of said instrument, means for modifying said value based on parameters relating to the use of the odontological instrument and means for indicating that a limit value is reached.

According a preferred embodiment of the device of the invention, said means indicating a value representing the current fatigue of said instrument comprise a washer.

According to a first embodiment said washer is provided with a predetermined number of pre-perforations.

According to a second embodiment said washer comprises a predetermined number of detachable protrusions.

According to a special embodiment of the device of the invention said means indicating a value representing the current fatigue of said instrument comprises a code for identifying said instrument on an univocal way and for associating a value representing the current fatigue, and in that the device comprises a storage device for memorizing the current fatigue of each instrument.

According to an advantageous embodiment the device comprises a reading device for reading said code.

According to an advantageous embodiment the device comprises a stop washer said code being placed on said stop washer.

Said code is advantageously a bar-code.

Another object of the invention is a method for indication the current fatigue of a odontological instrument having at least a cutting zone and a handle, characterized in that it comprises a step of determining the value of current fatigue of the odontological instrument, a step of determining the value of fatigue corresponding to a specific use, depending of operational parameters of the instrument, a step of modifying the value representing the current fatigue according to the value of the fatigue induced by a specific use, depending of operational parameters of the instrument, a step of comparing the new modified value representing the new current value of fatigue of the instrument with a limit value.

According an advantageous embodiment of the device of the invention the curve radius of the dental canal is taken as an operational parameter of the instrument.

According another advantageous embodiment of the device of the invention the taper ratio of the instrument is taken as a operational parameter of the instrument.

According an advantageous embodiment of the device of the invention the duration of the operation corresponding to said specific use is taken as a operational parameter of the instrument.

According to a first manner to apply the method in which the odontological instrument comprises a washer provided with a number of pre-perforations the step of determining the value of current fatigue of the odontological instrument consists in realizing a number of perforations, this number depending of the value representing fatigue induced by the specific use.

According to a second manner to apply the method in which the odontological instrument comprises a washer provided with a number of detachable protrusions, the step of determining the value of current fatigue of the odontological instrument consists in detaching a number of protrusions, this number depending of the value representing fatigue induced by the specific use.

According to a third manner to apply the method in which the odontological instrument comprises a code, the step of modifying the value representing the current fatigue consists in modifying the value representing the current fatigue in the storage device, according to the value representing the fatigue induced by the specific use.

DETAILED DESCRIPTION OF THE INVENTION

Figure 1:
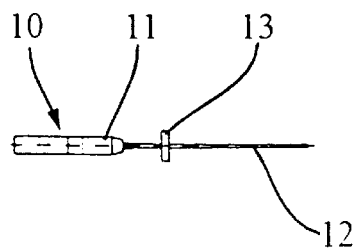
FIG. 1 is a lateral view of an instrument to excavate a dental canal according to the prior art.
Figure 2:
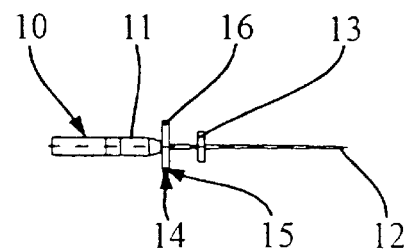
FIG. 2 is a lateral view of an instrument to excavate a dental canal according to a first embodiment of the device of the invention.
Figure 3:
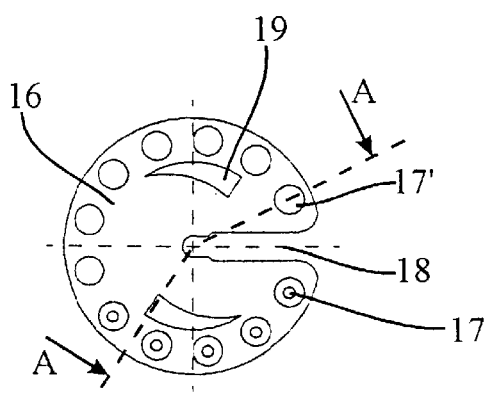
FIG. 3 is an enlarged front view of a washer according to a first embodiment of the device of the invention.
Figure 5:
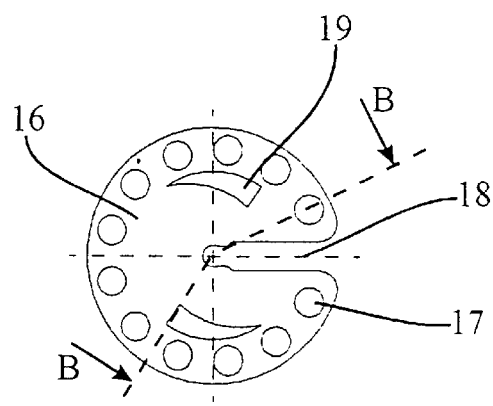
FIG. 5 is an enlarged front view of the washer according a second embodiment of the device of the invention.
Figure 4:
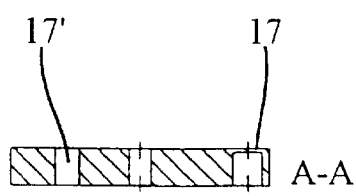
FIG. 4 is a sectional view along the line A—A of FIG. 3.
Figure 6:
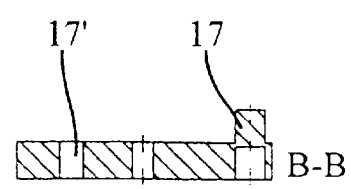
FIG. 6 is a sectional view along the line B—B of FIG. 5.

The FIG. 1 shows a odontological instrument 10 as it is used with the device of the present invention. The device 10 is provided with a handle 11, a cutting zone 12 or a blade whose operational length can be limited by a stop washer 13. The stop washer 13 is slidingly mounted on the cutting zone. It can also be suppressed. Depending from the use of the odontological instrument the cutting zone 12 may be tapered, the taper ratio being generally comprised between two and five degrees.

As shown by the FIGS. 2 to 10, the device 14 of the invention is provided with means 15 connected to the odontological instrument which are designed to indicate a value representing the current fatigue of this instrument, means to modify this value according to parameters depending of the use of the odontological instrument and means to indicate that a limit value is reached.

The means 15 for indicating the current value of fatigue comprise a washer 16. According to the embodiments shown by the FIGS. 3 to 6 the washer comprises pre-perforations 17. As long as the instrument is not used, the current fatigue having a zero value all the pre-perforations are intact.

When the surgeon uses the instrument for a specific operation he makes a valuation of the fatigue induced by the operation on the instrument. This valuation depends of various use parameters of the instruments during the operation, especially the curve radius of the dental canal to be excavated, the taper ratio of the instrument and the duration of the operation.

A fatigue value is attached to the fatigue in accordance with the operation which is performed by the surgeon: According to the embodiments represented by the figures, the value may vary between one and twelve, one corresponding to a very low fatigue and twelve to the highest fatigue. The fatigue value corresponds to the number of pre-perforations 17 that the surgeon must perforate in the washer. The reference 17' on the FIGS. 4 and 5 corresponds to the perforations made by the surgeon as a consequence of the use of the instrument for a given operation.

According to the fatigue value corresponding to a specific operation and to the current value of fatigue of the instrument, the surgeon can decide if the instrument is still adapted to perform the planned operation. If the number of pre-perforations which are still intact on the washer before the planned operation is less than the value of fatigue corresponding to that operation, the instrument cannot be used without a risk of rupture. Another instrument must be used.

According to the embodiments shown by the FIGS. 3 to 6 the washer comprises a notch 18 and two arrows 19. These elements are designed to indicate the starting point and the direction of the decrementation. It is therefore possible to avoid to pierce all the pre-perforations and to pierce only the last one. In the case when the fatigue corresponding to a specific operation is six, it would be possible to pierce only the sixth pre-perforation, without piercing all the five previous pre-perforations. Even this solution is not required it may represent a simplification for using the device of the invention.

Figure 7:
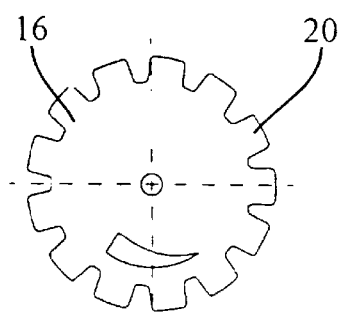
FIGS. 7 to 9 are front views showing various embodiments of the washer of the device of the invention.
Figure 8:
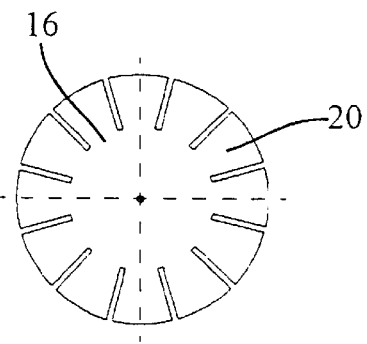
Figure 9:
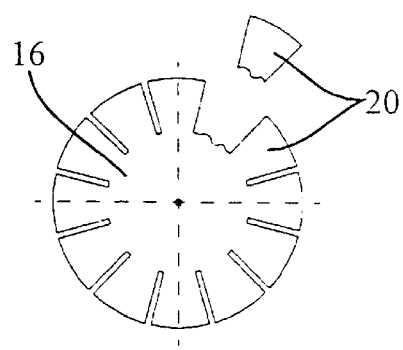
Figure 12:
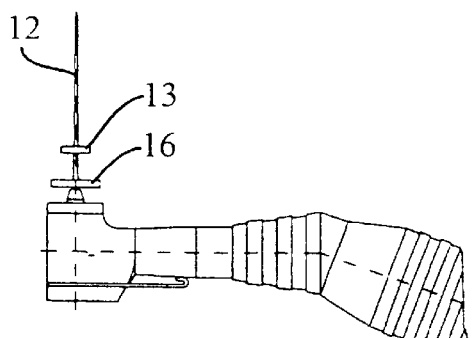
FIG. 12 a dental canal excavation instrument connected to a dental surgical drill.

The FIGS. 7 to 9 show diverse embodiments of the device of the invention, in which the information corresponding to the current value of fatigue is represented by a number of detachable protrusions 20. These protrusions are located along the periphery of the washer 16 and may be realized by an extrusion or a stamping operation.

The base part of these protrusions have a zone of reduced resistance so that each of them can be easily detached by a surgeon with a conventional tool as a pair of pliers for example. The number of the remaining protrusions correspond to the actual fatigue of the instrument.

These embodiments permit to visualize immediately the current fatigue of a odontological instrument.

Figure 10:
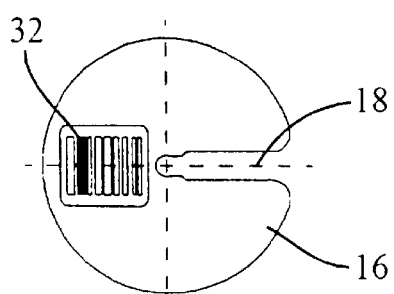
FIG. 10 is a front view showing a washer according to another embodiment of the device of the invention.
Figure 11:
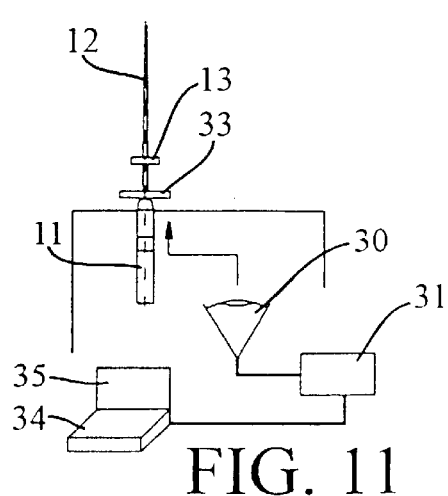
FIG. 11 shows schematically the use of the device of the invention provided with a washer as represented by FIG. 10.

The FIGS. 10 and 11 show another embodiment of the device of the invention in which the information relating to the current fatigue may be disclosed by means of an electronic code reading apparatus 30, for example a bar code reading device. This type of embodiment is particularly adapted for instruments having a very high rotation speed whereby the broken protrusions of the washer may create vibrations of the drill. For this kind of device the information relating to the fatigue is not storaged in the instrument but in a separated memory device 31.

A bar code 32 is attached to the instrument and located on the stop washer 13 (see FIG. 1) or on another washer 33 connected to the instrument. The bar code 32 comprises at least one pre-perforation designed to identify the corresponding instrument.

The memory device 31 contains for each instrument a value representing the current value of fatigue of said instrument and a limit value which must not be exceeded.

Before using an instrument for a given operation the surgeon valuates the fatigue of the instrument. He will transmit this value to a processor 34 which reads the fatigue value of the instrument, modifies this value according to the valuated value and compares the modified value to the limit value.

If the modified value is less than the limit value, the instrument can be used for the planned operation. If that value is higher, it must be used for another operation inducing a lower fatigue. The current value can be displayed by adequate means like a screen 35 of a computer or a liquid crystal screen.

According to the above embodiment the fatigue value may be decremented from an origin value, for example twelve to a limit value, for example zero. Otherwise, it may also be incremented from an origin value for example zero to an end or limit value for example one hundred. Such an embodiment would allow to provide a much more finer subdivision of the fatigue value. Contrarily to the embodiments of FIGS. 2 to 9 there are no geometrical restrictions for the representation of the limit value of fatigue.

To display a liable information the washer must be attached rigidly to the instrument and an accidental separation of both parts must be impossible. Furthermore the washer must be endure sterilization operations of the instrument in such a way that the relating information concerning fatigue does not risk to be loosed. Silicone is known as an appropriate material adapted to endure all these strains.

The washer may comprise indications for rendering easier the valuation of the fatigue by the surgeon. The color of the washer may represent such an indication corresponding for example to the taper ratio of the instrument.

Means 15 for indicating the value of the current fatigue are represented by a washer. Other elements may be adapted for the same function if they do not induce vibrations to the drill during the operation. Said means 15 are provided on a washer 16 which is independent from the stop washer 13. The washer 16 and the stop washer 13 could be replaced by a single washer integrating both functions.

In the embodiments of FIGS. 10 and 11 the code is a bar code: Other types of information coding means may be integrated in the washer 16. In such a case an adequate reading device must be used for reading the coded information.

What is claimed is:

1. A device for indication a current fatigue of an odontological instrument having at least a cutting zone (12) and a handle (11), wherein the device comprises:
   means connected to said odontological instrument (10) indicating a value representing the current fatigue of said instrument;
   means for modifying said value based on parameters corresponding to the use of the odontological instrument; and
   means for indicating when a limit value is reached.

2. The device according to claim 1, wherein said means for indicating (15) a value representing the current fatigue of said instrument (10) comprises a washer (16).

3. The device according to claim 2, wherein said washer (16) is provided with a predetermined number of pre-perforations (17).

4. The device according to claim 2, wherein said washer (16) comprises a predetermined number of detachable protrusions (20).

5. The device according to claim 1, wherein said means for indicating (15) a value representing the current fatigue of said instrument (100) comprises a code (32) for identifying said instrument on an univocal way and for associating a value representing the current fatigue, and the device comprises a storage device (31) for memorizing the current fatigue of each instrument.

6. The device according to claim 5, wherein said means for indicating (15) a value representing the current fatigue of said instrument (10) comprises a reading device (30) for reading said code (32).

7. The device according to claim 5, wherein said means for indicating (15) a value representing the current fatigue of said instrument (10) comprises a stop washer (13) and said code (32) is attached to said stop washer.

8. The device according to claim 5, wherein said code (32) is a bar-code.

9. A method for indication a current fatigue of an odontological instrument having at least a cutting zone and a handle, wherein the method comprises the steps of:
   determining a value of the current fatigue of the odontological instrument;
   determining the value of fatigue corresponding to a specific use, depending of operational parameters of the instrument,
   modifying the value representing the current fatigue according to the value of the fatigue induced by a specific use, depending from operational parameters of the instrument,
   comparing the new modified value representing the new current value of fatigue of the instrument with a limit value.

10. The method according to claim 9, further comprising the step of taking a radius of a dental canal as an operational parameter of the instrument.

11. The method according to claim 9, further comprising the step of taking a taper ratio of the instrument as an operational parameter of the instrument.

12. The method according to claim 9, further comprising the step of taking a duration of the operation corresponding to said specific use as an operational parameter of the instrument.

13. The method according to claim 5, further comprising the step of using an odontological instrument (10) which comprises a washer (16) provided with a number of perforations (17), wherein the step of determining the value of current fatigue of the odontological instrument comprises realizing a number of perforations (17), in which the number of perforations (17) depends on the value representing fatigue induced by the specific use.

14. The method according to claim 9, further comprising the step of using an odontological instrument (10) which comprises a washer (16) provided with a number of detachable protrusions (20), wherein the step of determining the value of current fatigue of the odontological instrument comprises detaching a number of protrusions/(20), in which the number of protrusions (20) depends on the value representing fatigue induced by the specific use.

15. The method according to claim 9, further comprising the step of using an odontological instrument (10) which comprises a code (32), wherein the step of modifying the value representing the current fatigue comprises modifying the value representing the current fatigue in the storage device (31), according to the value representing the fatigue induced by the specific use.

* * * * *